United States Patent
Chen

(10) Patent No.: US 7,147,641 B2
(45) Date of Patent: Dec. 12, 2006

(54) FIXATION ELEMENT INSERTION DEVICE

(76) Inventor: Michael C. Chen, 923 Bill Smith Blvd., King of Prussia, PA (US) 19406

(*) Notice: Subject to any disclaimer, the term of this patent is extended or adjusted under 35 U.S.C. 154(b) by 646 days.

(21) Appl. No.: 09/866,841

(22) Filed: May 30, 2001

(65) Prior Publication Data

US 2002/0193807 A1    Dec. 19, 2002

(51) Int. Cl.
*A61B 17/56* (2006.01)

(52) U.S. Cl. ............................... 606/72; 606/104

(58) Field of Classification Search ............. 606/151, 606/213, 219, 72, 104; *A61B 17/04*
See application file for complete search history.

(56) References Cited

U.S. PATENT DOCUMENTS

| | | | | |
|---|---|---|---|---|
| 4,402,641 A | 9/1983 | Arff | ............ | 411/510 |
| 4,776,328 A | 10/1988 | Frey et al. | ............ | 128/92 VT |
| 4,776,739 A | 10/1988 | Hamman | ............ | 411/510 |
| 4,963,144 A | 10/1990 | Huene | ............ | 606/73 |
| 5,071,420 A | 12/1991 | Paulos et al. | ............ | 606/99 |
| 5,139,499 A | 8/1992 | Small et al. | ............ | 606/73 |
| 5,236,431 A | 8/1993 | Gogolewski et al. | ............ | 606/72 |
| 5,258,016 A | 11/1993 | DiPoto et al. | ............ | 606/232 |
| 5,261,914 A | 11/1993 | Warren | ............ | 606/73 |
| 5,268,001 A | 12/1993 | Nicholson et al. | ............ | 606/72 |
| 5,391,170 A | 2/1995 | McGuire et al. | ............ | 606/86 |
| 5,445,641 A | 8/1995 | Frigg et al. | ............ | 606/86 |
| 5,522,843 A | 6/1996 | Zang | ............ | 606/232 |
| 5,578,057 A | 11/1996 | Wenstrom, Jr. | ............ | 606/232 |
| 5,584,860 A | 12/1996 | Goble et al. | ............ | 606/232 |
| 5,590,574 A | 1/1997 | Lide | ............ | 81/124.1 |
| 5,672,038 A | 9/1997 | Eaton | ............ | 411/510 |
| 5,683,401 A | 11/1997 | Schmieding et al. | ............ | 606/104 |
| 5,720,766 A | 2/1998 | Zang et al. | ............ | 606/232 |
| 5,735,854 A | 4/1998 | Caron et al. | ............ | 606/73 |
| 5,741,268 A | 4/1998 | Schütz | ............ | 606/104 |
| 5,800,109 A | 9/1998 | Carruthers | ............ | 411/510 |
| 5,814,051 A | 9/1998 | Wenstrom, Jr. | ............ | 606/104 |
| 5,893,856 A | 4/1999 | Jacob et al. | ............ | 606/151 |
| 5,895,396 A | 4/1999 | Day et al. | ............ | 606/151 |
| 5,901,424 A | 5/1999 | Rector | ............ | 27/21.1 |
| 5,904,685 A | 5/1999 | Walawalkar | ............ | 606/73 |
| 5,906,624 A | 5/1999 | Wenstrom, Jr. | ............ | 606/139 |
| 6,007,539 A | 12/1999 | Kirsch et al. | ............ | 606/75 |

FOREIGN PATENT DOCUMENTS

| | | |
|---|---|---|
| DE | 29 33 141 | 4/1980 |
| EP | 0 834 281 A1 * | 4/1998 |
| EP | 1 090 591 A2 | 4/2001 |
| EP | 1 090 591 A3 | 4/2001 |
| FR | 2 682 587 | 4/1993 |
| FR | 2 777 443 | 10/1999 |

* cited by examiner

*Primary Examiner*—Henry Bennett
(74) *Attorney, Agent, or Firm*—Morgan, Lewis & Bockius LLP

(57) ABSTRACT

The invention relates to a device for attaching fixation elements to bone, having a longitudinal member with a channel extending therein adapted for receiving at least one fixation element. A shaft extends within the channel and is positioned coaxially within at least a portion of the longitudinal member and at least a portion of the shaft is retained within the longitudinal member and a distal end of the shaft is configured and adapted to contact at least a portion of the fixation element received within the longitudinal member. The longitudinal member is moveable with respect to the shaft to drive the fixation element into bone.

28 Claims, 7 Drawing Sheets

FIXATION ELEMENT INSERTION DEVICE

FIELD OF THE INVENTION

The present invention relates to a device for the storage and dispensing of osteosynthetic fixation elements, and in particular to a device for attaching fixation elements to bone.

BACKGROUND OF INVENTION

In the surgical treatment of fractures in the maxillofacial area, as well as fractures of the foot and hand, a trend toward preferring ever-smaller implants can clearly be noted. The reason for this is the generally increased understanding of the biomechanical bases of osteosynthesis. In the field of treating maxillofacial fractures, more attention can be paid to the cosmetic results of osteosynthesis, thanks to the miniaturization of implants. In the field of hand surgery, restrictions on movement in the area of the fingers can be avoided. In this regard, smaller osteosynthetic implants in the fingers can be placed under the tendons. In the case of an implant with a large cross-section, the tendons need no longer be extended to their full length.

The dimensions of some smaller implants (screws, plates and tacks) are in the range of about 0.8 mm to about 2.0 mm. Problems in the area of packaging, storage and manipulation during surgery arise due to this miniaturization. Handling in the operating room, particularly in the maxillofacial area, has proved difficult. Depending on the degree of severity of the fracture or correction, up to 40 bone fixation elements, such as tacks or screws, may be required. These screws must be taken individually by the operating room nurse from a so-called screw rack, checked for length, placed on a screwdriver and given to the surgeon. The surgeon must, in turn, insert them through the osteosynthesis plate into pre-drilled screw holes. During the transfer of the screw and the attempted insertion of the screw, it often falls off the screwdriver, into the wound or onto the operating room floor. The attempt to find a lost screw is often excessively time-consuming, given their dimensions and extends the time spent in surgery. The frequent loss of screws in the operating room, and during packing and sterilization, causes unnecessary costs for the hospital.

An additional problem in dealing with mini-screws arises during their implantation. After the surgeon has selected the osteosynthesis plate proper for the fracture in question, a plate is positioned over the fracture. A hole is then drilled for the screw (0.5–1.5 mm diameter) through one of the plate holes. After drilling, the screw is received from an operating room nurse and screwed into the bone through the plate. Commonly problems arise in finding the core drill hole in the bone, since the bone surface is covered with blood or soft tissue and the plate can slip on the smooth bone surface.

SUMMARY OF INVENTION

The present invention relates to a device for attaching fixation elements to bone, including a longitudinal member extending along a longitudinal axis from a proximal end to a distal end and having a channel extending therein adapted for receiving at least one fixation element. A shaft extends within the channel and is positioned coaxially within at least a portion of the longitudinal member and at least a portion of the shaft is retained within the longitudinal member and a distal end configured and adapted to contact at least a portion of the fixation element received within the longitudinal member. The longitudinal member is moveable with respect to the shaft to drive the fixation element into bone.

In one embodiment, the longitudinal member can include a first member for receiving at least one fixation element at the distal end and a second member attached coaxially to the first member, and the first member is movable with respect to the second member. A spring can be housed within the channel to engage the first member for resiliently biasing the first member in the axial direction. In one preferred embodiment, the first and second members are substantially cylindrical and the first member is movable telescopingly within the second member. The first and second members can be interlocked in the axial direction. The shaft is substantially cylindrical and can have at least two portions with different diameters. The distal end of the longitudinal member includes a pronged tip for resiliently holding a fixation element therein.

Another device for attaching fixation elements to bone according to the present invention comprises a longitudinal member having a channel extending therein and a plurality of spacers positionable within the channel. Each spacer has a tip portion at a distal end configured and dimensioned for holding a fixation element. In one embodiment, the spacer has a cavity at a proximal end configured and dimensioned for receiving a tip portion of an adjacent spacer. The spacer can have a frustoconical portion. The fixation element is held to the tip portion by a friction fit and the spacer has a shoulder at a base of the tip portion configured for contacting a proximal end of an adjacent spacer when such spacers are in abutting relationship. In one preferred embodiment, the spacers are stackable such that a plurality of spacers are positionable in abutting relationship and the spacers can be axially alignable within the channel.

In another embodiment, the device includes a shaft located centrally with respect to the channel for moving the spacers axially with respect to the shaft. The shaft can include a frustoconical tip at a distal end and the tip can be received in the proximal end of the spacer. In one embodiment, a tab extends radially outward from the shaft and is configured to be movable by a human finger to move the shaft with respect to the longitudinal member. A spring engages a slot in the longitudinal member for locating the shaft at a plurality of preselected locations with respect to the longitudinal member.

In one embodiment, the channel has a front opening at the distal end of the longitudinal member and the spacers can travel through the opening. The channel can also include a back opening at the proximal end of the longitudinal member and the spacer can travel through the back opening. A handle is connected to the proximal end of the longitudinal member.

The present invention is also directed to a device for holding a fixation element, including a holding portion configured to hold the fixation element, and a receiving portion connected to the holding portion and configured to receive an adjacent fixation element holder and fixation element. The holding portion is configured to releasably hold the fixation element and the receiving portion can include a body having a cavity therein. The holding portion has an exterior contour and the interior cavity has an internal contour, and the interior contour is configured and dimensioned to conform to the exterior contour.

DETAILED DESCRIPTION OF THE PREFERRED EMBODIMENTS

Figure 1:
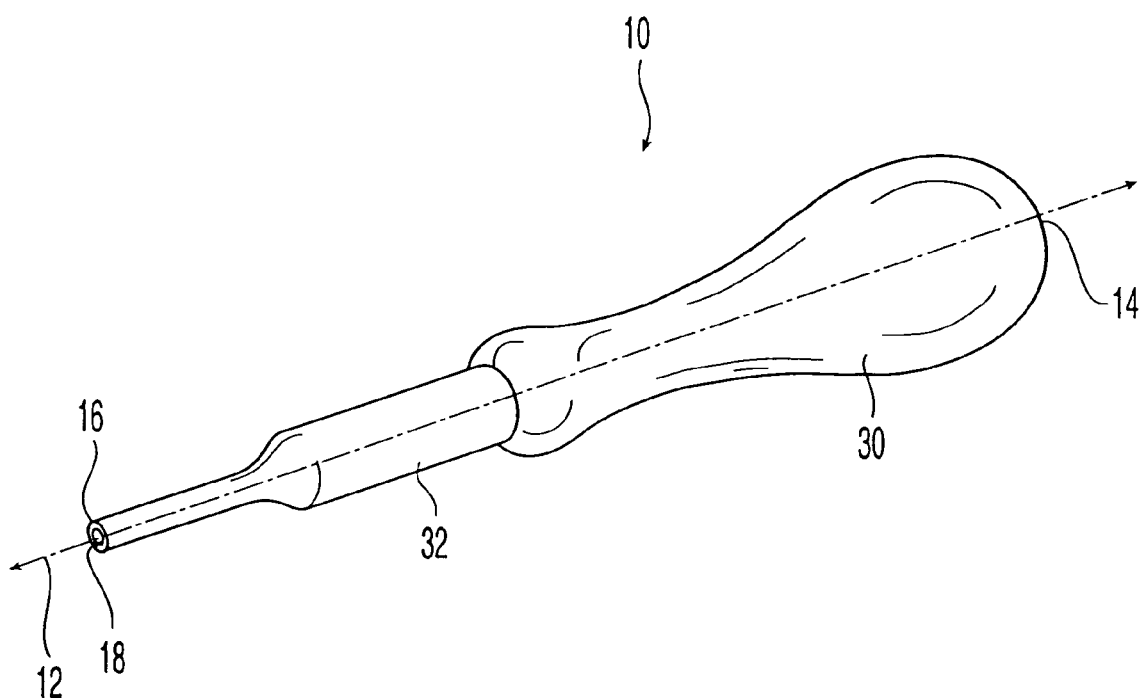
FIG. 1 is a perspective view of one embodiment of an insertion device according to the present invention.

Referring to FIG. 1, a preferred fixation element insertion device 10 according to the present invention generally includes a longitudinal member extending along a longitudinal axis 12 from a proximal end 14 to a distal end 16 and having a channel 18 extending therein. The insertion device is preferably used to drive an osteosynthetic fixation element, such as a resorbable tack, into bone tissue. Channel 18 is configured and dimensioned to receive at least one fixation element for storage, transport, dispensing, and or insertion into bone.

Figure 2:
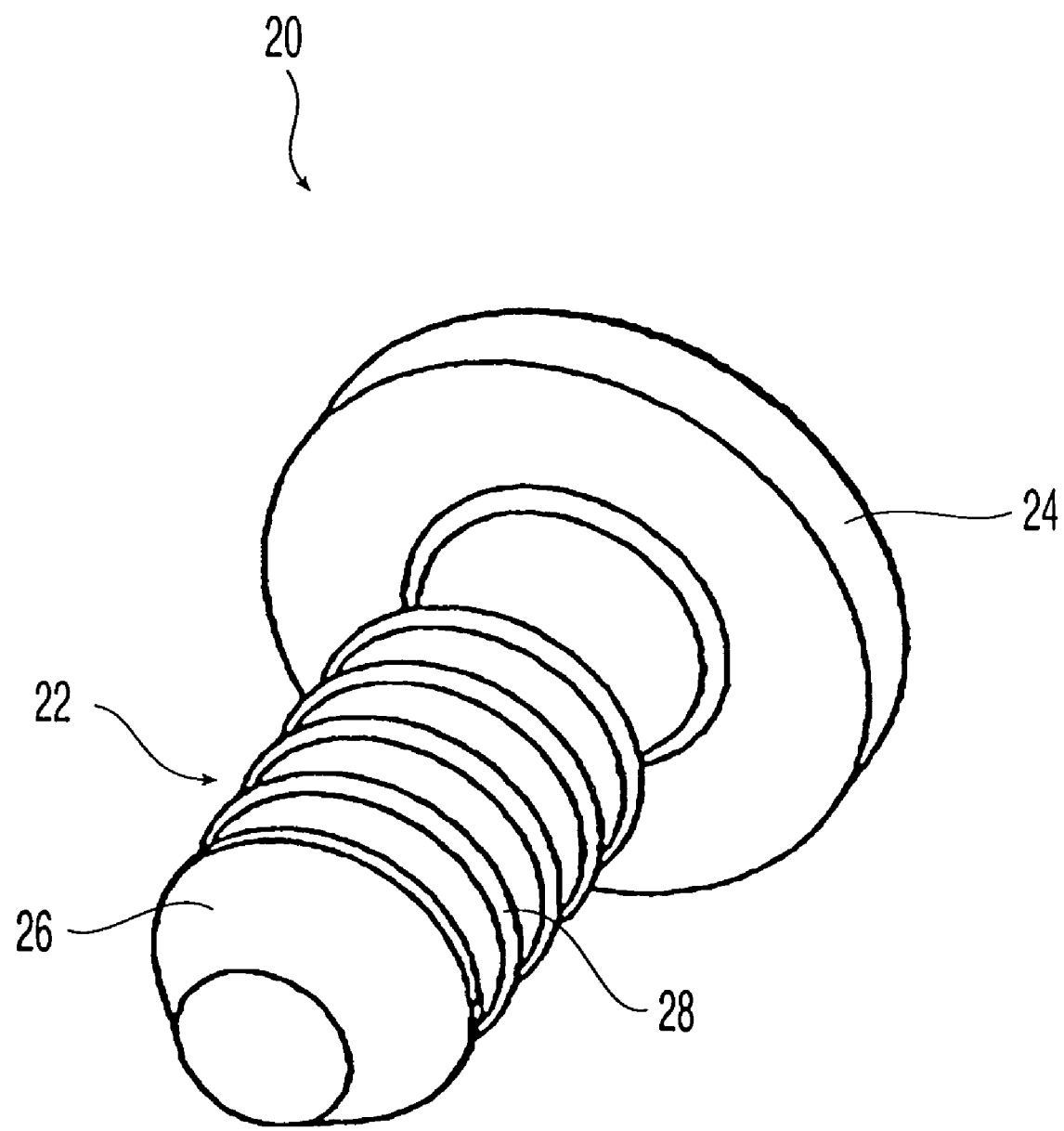
FIG. 2 is a perspective view of a fixation element for use with the insertion device of FIG. 1.

Referring to FIG. 2, one preferred fixation element compatible with insertion device 10 comprises a tack 20 having a shaft 22 integral with a head 24 at a proximal end thereof. The distal end of shaft 22 has a conical nose 26 to facilitate the insertion of tack 20 into bone tissue. A plurality of circular ribs 28 extend radially from the exterior of shaft 22 to prevent the removal of the tack from the bone tissue after it has been inserted. Head 24 has an outer diameter greater than the diameter of shaft 22 and contacts or rests against the bone or bone plate when the tack is inserted into bone tissue. In the preferred embodiment, the tack is made from a resorbable material so that it remains in the bone tissue temporarily and is absorbed by the body. In alternate embodiments, tack 20 can have numerously different configurations and dimensions. Also, different types of fixation elements altogether can be used with insertion device 10. For example, biocompatible screws, nails, anchors, rivets, or other similar implants can also be inserted using insertion device 10.

Referring again to FIG. 1, insertion device 10 has a handle 30 at the proximal end that is configured to conform to the shape of a person's hand or palm for easily gripping and applying force with the device. Channel 18 generally comprises a socket defined at the distal end 16 and an elongate applicator extension 32 extends between distal end 16 and handle 30. Socket or channel 18 fits about the proximal end of fixation element 20 to hold element 20 in insertion device 10 by an interference or friction fit. In the embodiment of FIG. 1, an individual tack 20 can be held at distal end 16 and head 24 of tack 20 is preferably held within the socket or channel 18 while the shaft 22 of tack 20 projects outside thereof, as shown in FIG. 3.

Figure 4:
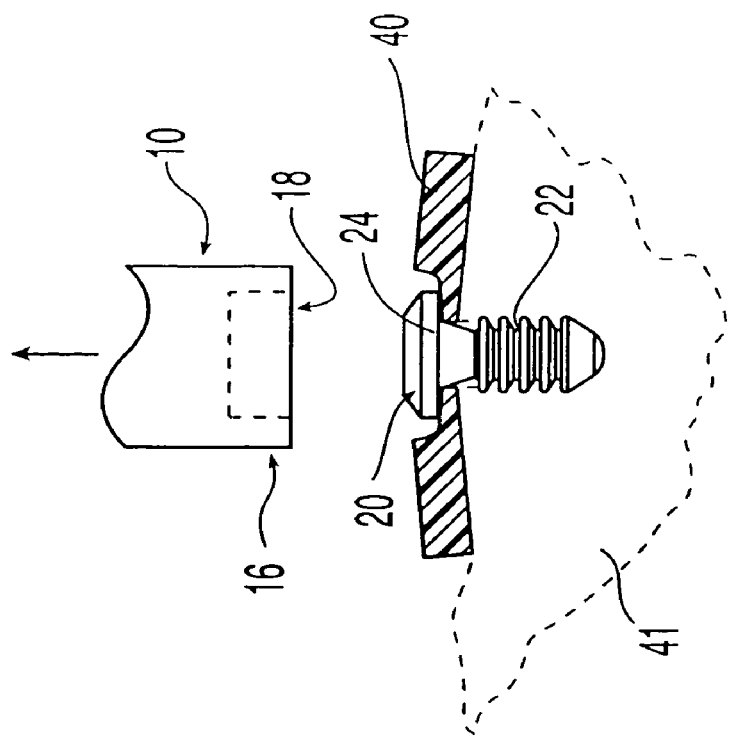
FIGS. 3–4 illustrate the placement of a fixation element within a pre-drilled hole in bone.
Figure 3:
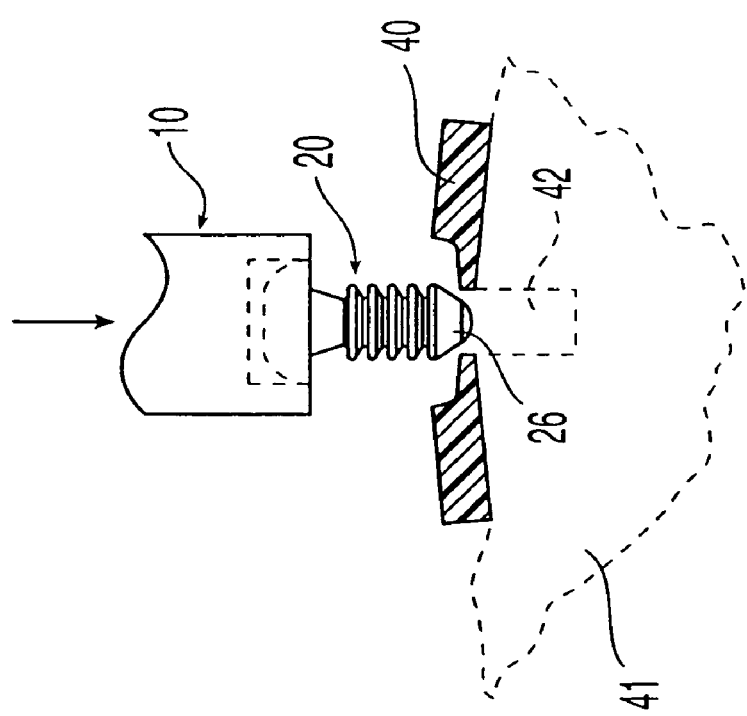

Referring to FIGS. 3–4, the insertion device can be used to fasten a plate 40 or other device to a bone 41. In operation, a hole 42 is pre-drilled in the bone tissue at the desired insertion location and the insertion device 10 is placed adjacent the insertion location and the conical nose 26 of tack 20 is inserted into hole 42 and then shaft 22 of tack 20 is driven into the bone tissue by applying force in the axial direction to the handle, such as by a person's hand. As shown in FIG. 4, once tack 20 is inserted into bone, insertion device 10 is withdrawn from the insertion location and tack 20 is separated from channel 18. When the insertion device 10 is withdrawn, the forces holding shaft 22 of tack 20 to bone 41 are greater than the forces of the interference fit between head 24 and channel 18 so that head 24 of tack 20 is separated from distal end 16, leaving tack 20 secured to the bone. In a preferred embodiment, insertion device 10 is a reusable device and is autoclavable between uses.

Figure 5:
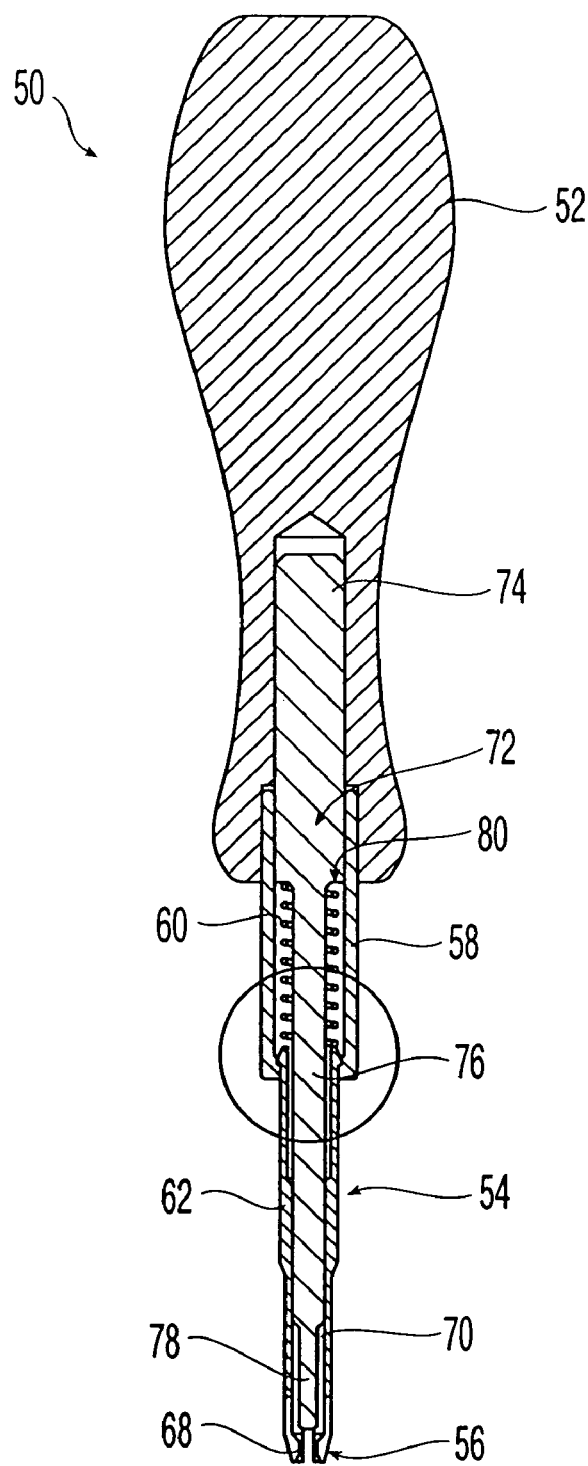
FIG. 5 is a cross-sectional view of another embodiment of an insertion device.
Figure 6:
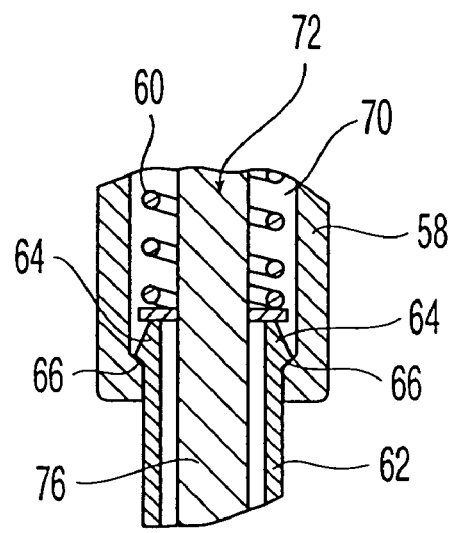
FIG. 6 is a partial cross-sectional view of a portion of the device of FIG. 5.

Referring to FIGS. 5–6, an alternate embodiment of an insertion device 50 includes a handle 52 at a proximal end and a spring loaded elongate applicator extension 54 extending between distal end 56 and handle 52. Extension 54 comprises a spring cover 58 attached to handle 52 for housing spring 60 and a holding sleeve 62 coaxially attached to the distal end of spring cover 58 in a telescoping fashion for receiving a fixation element. Sleeve 62 has slightly smaller external dimensions than the internal dimensions of cover 58 so that the proximal end of sleeve 62 can be inserted into the distal end of cover 58 and sleeve 62 can move in the axial direction with respect to cover 58. Sleeve 62 includes prongs 64 that interlock with ridges 66 on the interior of cover 58 so that when sleeve 62 is inserted into cover 58, sleeve 62 is not inadvertently removed from cover 58 in the distal direction. In a preferred embodiment, sleeve 62 has prongs 64 that are flexible and are collapsible or bendable into the interior of sleeve 62 so that sleeve 62 can be removed from cover 58 for cleaning, disassembly, or replacement. Prongs 64 are biased radially outwardly so that sleeve 62 can be easily reattached by simply pushing the sleeve into the cover in the proximal direction. At the distal end of sleeve 62 is a pronged tip for retaining a fixation element. Pronged tip 68 is generally flexible and when the distal end of sleeve 62 is pressed, the prongs of sleeve 62 flex around the head of a fixation element to pick up and retain the element. In this way, it is possible to pick up a relatively small fixation element in a simple, single action.

A central channel 70 extends within handle 52 and through extension 54. A shaft member 72 is housed within central channel 70 and extends generally the entire length of channel 70 within extension 54 and is preferably fixedly attached to handle 52. Shaft 72 is generally cylindrical and includes a base portion 74 that engages the interior of channel 70 within handle 52 preferably by press fit, a mid-section 76 having a smaller diameter than base portion 74, and a tip portion 78 having a smaller diameter than mid-section 76. A first shoulder 80 is positioned at the transition of base portion 74 and mid-section 76. Spring 60 is housed within spring cover 58 and extends around mid-section 76 and is compressible between first shoulder 80 and the proximal end of sleeve 62, biasing sleeve 62 axially in the distal direction.

The method of operation or use of device 50 is similar to the method described above with respect to device 10. The insertion device 50 is placed adjacent an insertion location with a pre-drilled hole in bone and the fixation element or tack is driven into the bone tissue by applying axial force in the distal direction to handle 52, moving sleeve 62 in the proximal direction. When sleeve 62 is moved in the proximal direction, spring 60 biases sleeve 62 in the distal direction and shaft 72 is moved in the distal direction due to the force applied on the handle. Thus, when sleeve 62 is moved further in the proximal direction, such as by applying axial force in the distal direction during fixation element insertion, sleeve 62 is retracted within cover 58 and shaft 72 is forced in the distal direction through the distal end of sleeve 62. Tip portion 78 of shaft 72 engages the proximal end of a fixation element and separates the fixation element from pronged tip 68 and drives the fixation element into bone. In this way, the fixation element is automatically disengaged from distal end 56 of device 50 and there is no need to manually slide holding sleeve 58 or rock the insertion device to disengage the fixation element. After the fixation element has been inserted completely, insertion device 50 can be removed from the insertion location and sleeve 62 will spring back to its original starting position, shown in FIG. 5. In an alternate embodiment, shaft 72 is moveable in the axial direction with respect to handle 52.

Figures 7, 8:
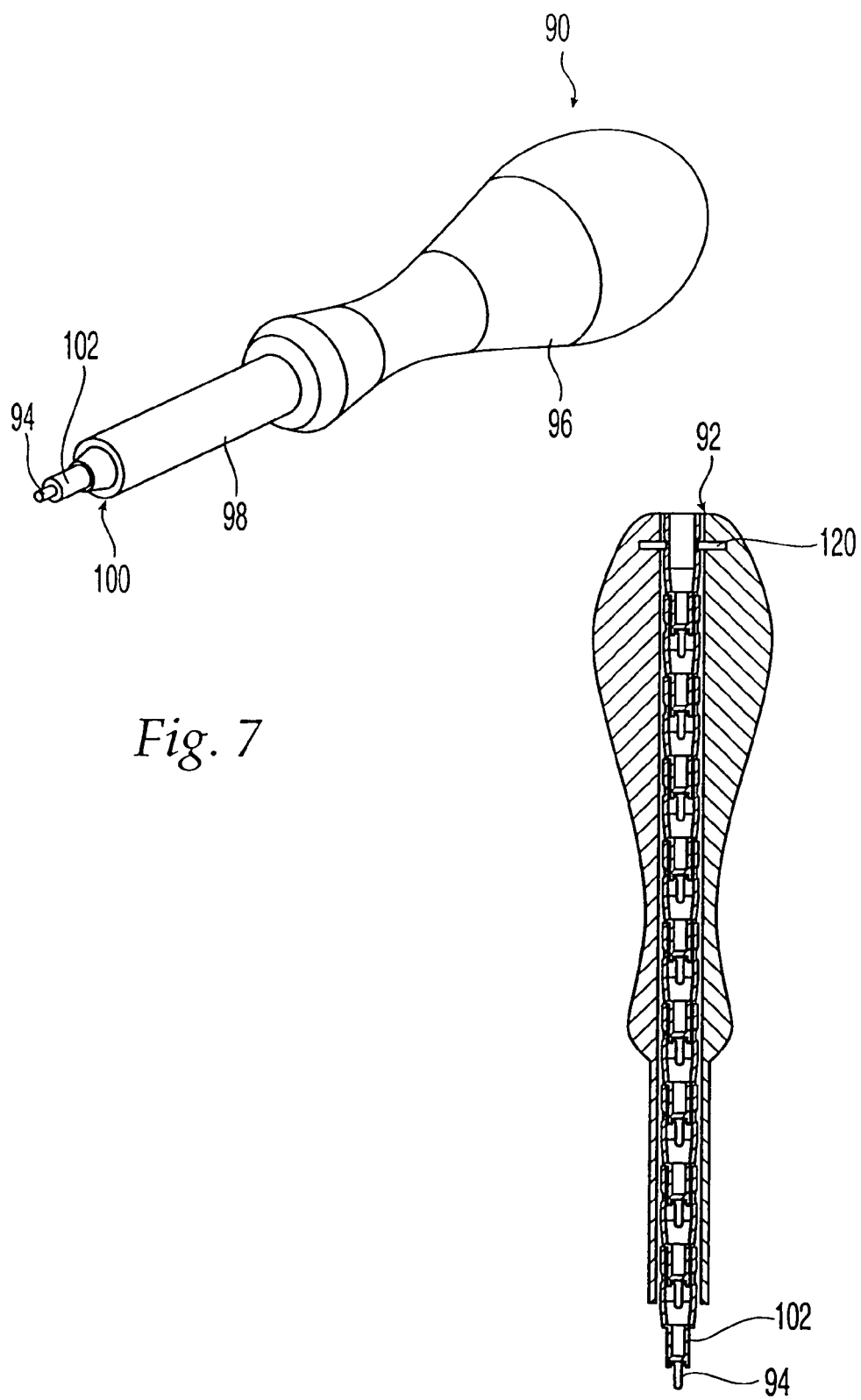
FIG. 7 is a perspective view of another embodiment of an insertion device.
FIG. 8 a cross-sectional view of the embodiment of FIG. 7.

Referring to FIGS. 7–8, an alternate embodiment of an insertion device 90 includes a central channel 92 that extends through device 90 for receiving fixation elements or tacks 94. Channel 92 can store a plurality of tacks 94 and when insertion device 90 is used, a sufficient supply of tacks are available for quick and easy insertion into bone. A handle 96 is at a proximal end of device 90 and an elongate applicator extension 98 extends between a distal end 100 and handle 96. Once a tack 94 is inserted into bone, another tack is advanced toward distal end 100 and into position to be inserted. In this way, a surgeon or nurse does not need to repeatedly attach or load fixation elements into an insertion device and there is a ready supply of fixation elements housed within the device. Thus, the device only needs to be loaded once, thereby reducing operating time.

Figure 9:
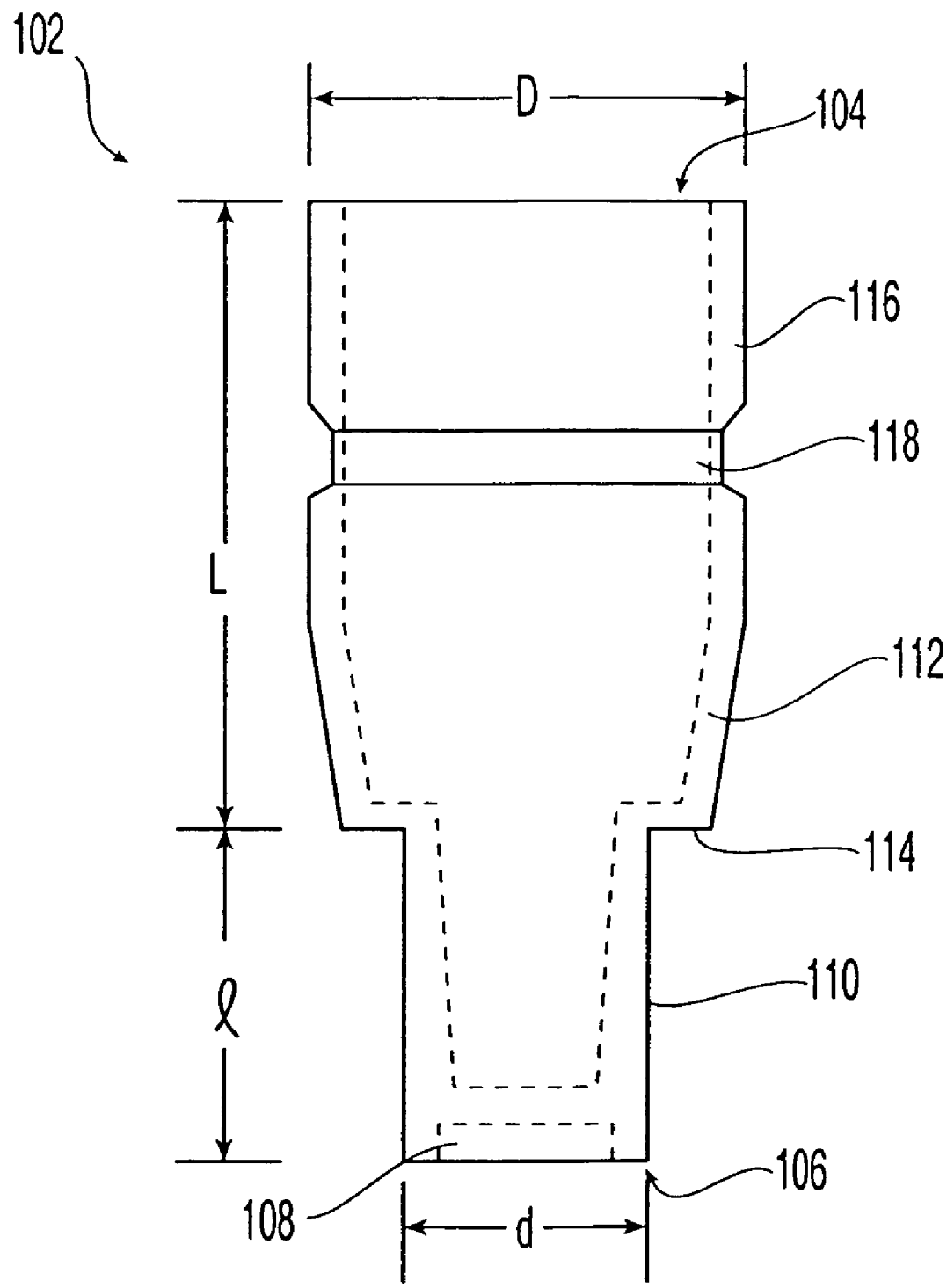
FIG. 9 is a side view of a fixation element spacer for use with the insertion device of FIG. 7.

In the preferred embodiment, the tacks are attached to carriers or spacers 102 and are aligned coaxially within the central channel 92 of device 90. In a preferred embodiment, spacer 102 is hollow and has an exterior contour and an interior contour, and the interior contour is generally configured and dimensioned to conform to the exterior contour so that a plurality of spacers are easily stacked. As best seen in FIG. 9, each spacer 102 has a circular cross section which tapers from a hollow proximal end 104 to a distal end 106 having a socket 108 for receiving a tack 94. Like the embodiment of FIG. 1, tack 94 is held in socket 108 by an interference or friction fit. Each spacer can accommodate at least one fixation element at the distal end, and a plurality of spacers can be inserted into central channel 92 of insertion device 90, each with a tack attached to the distal end. The spacers are aligned coaxially within central channel 92 such that each spacer 102 proximal end 104 is aligned to receive a distal end 106 of an adjacent spacer so that the spacers can be axially stacked in abutting relation within channel 92, as shown in FIG. 8. Each spacer 102 comprises a cylindrical nose or tip portion 110 toward distal end 106 and has a diameter d. Tip portion 110 extends an axial distance 1 from an angled mid-section portion 112. A shoulder 114 is formed at the intersection of tip portion 110 and mid-section portion 112. Back portion 116 extends from mid-section portion 112 and includes a slot 118 extending around the outer periphery. Back portion 116 is preferably substantially cylindrical having a diameter D and mid-section portion 112 is preferably substantially frusto-conical. Back portion 116 diameter D is larger than tip portion 110 diameter d so that tip portion 110 of a spacer 102 can be accommodated within the interior of back portion 116. In a preferred embodiment, shoulder 114 extends radially beyond the perimeter of tip portion 110 and is configured and dimensioned to rest against or abut the proximal end 104 of back portion 116. Mid-section portion 112 and back portion 116 extend an axial distance L from shoulder 114 to proximal end 104, and distance L is preferably greater than distance 1. In this way, when a fixation element or tack 94 is attached to a tip portion of a first spacer and then inserted into the interior of a proximal end of a second spacer, there is sufficient space within the interior of the second spacer to accommodate the tip portion of the first spacer and a fixation element attached thereto.

The spacers 102 are individually moveable within channel 92. For example, spacers 102 are advanced in the distal direction when an additional spacer is introduced into the proximal end of channel 92. When a spacer is inserted into the proximal end of channel 92, shoulder 114 of the spacer being inserted contacts the proximal end 104 of the most proximal spacer in channel 92 and pushes or forces all of the spacers in the channel in the axial direction toward distal end 100 of device 90. The most distal spacer extends from distal end 100 of driver 90 and the shaft of tack 94 extends beyond socket 108 of spacer 102 in a position ready to be inserted into bone. In the preferred embodiment, an elastic ring 120 is positioned on the interior of channel 92 adjacent the proximal end for engaging slot 118 to prevent movement of the spacers in the proximal direction. Ring 120 extends radially inward into channel 92 and engages slot 118 of the most proximal spacer, and when channel 92 is full of spacers, the spacers do not move in the proximal direction.

In operation of insertion device 90, a tack is inserted in the bone tissue by means of an axial force exerted on the proximal end of the device, much the same as for device 10 of FIG. 1. After the tack is inserted in the bone, the device is removed from the insertion location thus separating the element from the distal most spacer at the distal end of the device, and leaving the tack in the bone. In a preferred method, the now empty distal most spacer is then removed from the distal end of channel 92 and reinserted into the proximal end thereof, advancing the remaining spacers distally in the channel and moving the distal most spacer and tack to the distal end 100 of the device and ready to insert the tack. This method can be repeated as desired for the particular application. In a preferred embodiment, channel 92 is configured to accommodate about ten spacers, however the invention is also applicable to different size insertion devices with various channel lengths to accommodate more or less spacers or fixation elements as desired. Similarly, differing spacer dimensions or fixation element dimensions can also influence the fixation element holding capacity of the insertion device. Also, it is not required that empty spacers be introduced into the proximal end of channel 92, and spacers having tacks attached thereto can also be introduced, thereby providing a continuous supply of fixation elements.

Figure 10:
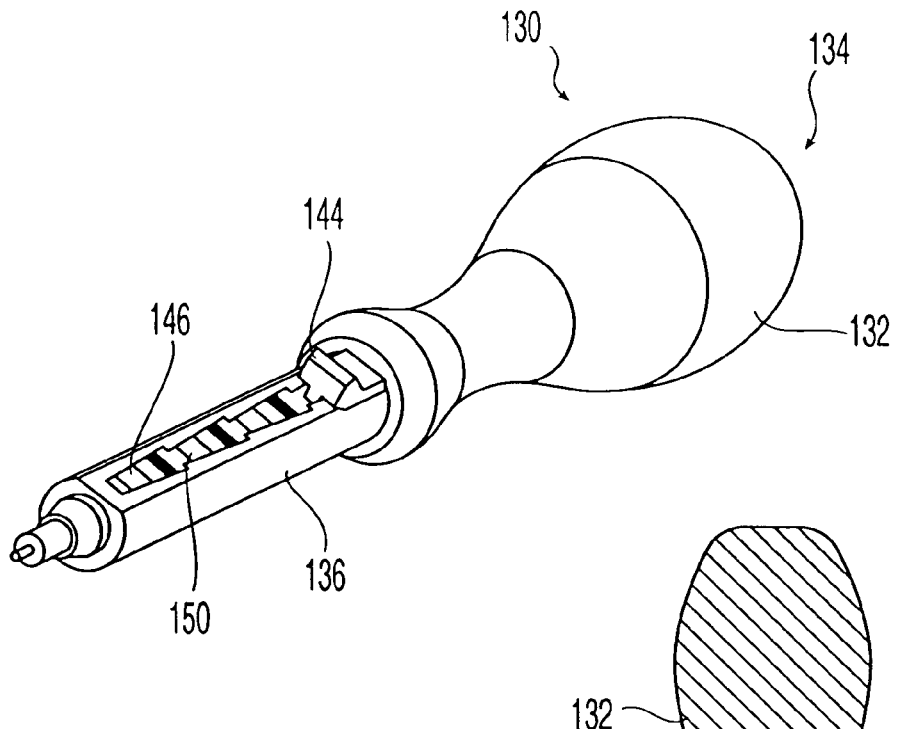
FIG. 10 is a perspective view of another embodiment of an insertion device.
Figure 11:
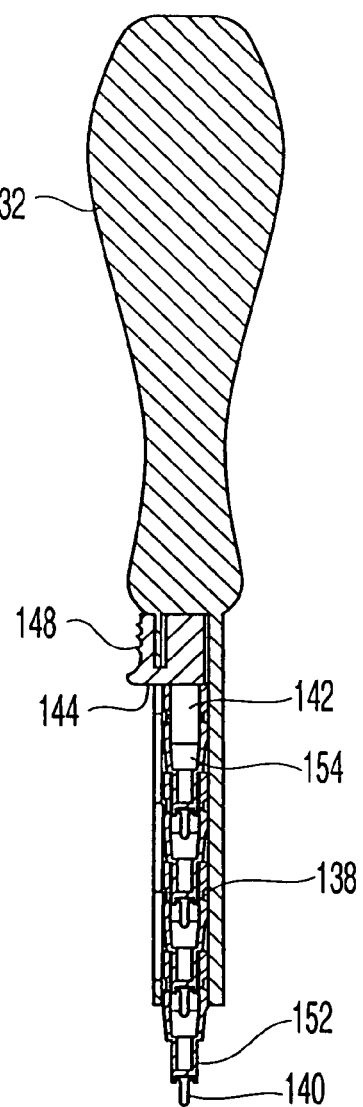
FIG. 11 is a cross-sectional view of the embodiment of FIG. 10.

Referring to FIGS. 10–11, an alternate embodiment of an insertion device 130 includes a handle 132 at the proximal end 134 and an elongate applicator extension 136 extends from handle 132 in the distal direction. Applicator extension 136 has a central channel 138 for receiving a plurality of fixation elements or tacks 140 and a piston 142 is axially aligned with channel 138 and movable therein to advance the tacks in the distal direction. Piston 142 is positioned at the proximal end of channel 138 and a tab 144 extends laterally from one side of piston 142 and through a longitudinal slot 146 in extension 136. Tab 144 includes a knurled or textured portion 148 for engaging a person's finger to allow for manual advancement of piston 142 within channel 138. In a preferred embodiment, slot 146 includes angled portions 150 and a spring (not shown) is attached to tab 144 to engage angled portions 150 of slot 146 and prevent piston 142 from moving in a proximal direction. Channel 138 forms a fixation element supply chamber, and like the insertion device of FIGS. 7–8, the fixation elements are attached to spacers 152 and are aligned coaxially within channel 138 to be inserted into bone tissue one at a time as described above. The configuration and design of the spacers 152 used with device 130 are the same as spacer 102 shown in FIG. 9. Also, the fixation elements are held at the distal end of each spacer by the same interference or friction fit used in the device of FIGS. 7–8. In a preferred embodiment, channel 138 is configured to accommodate about four spacers, however the invention is also applicable to different size insertion devices with various channel lengths to accommodate more or less spacers or fixation elements as desired.

In operation of insertion device 130, the distal end of piston 142 interfaces engages the proximal end of the last or proximal most spacer aligned within channel 138 to force the spacer in the distal direction and advance all of the aligned spacers in the channel. In a preferred embodiment, piston 142 exterior substantially corresponds to the interior of the mid-section and back portion of spacer 152. For example, piston 142 is preferably generally cylindrical with a tapered portion 154 at the distal end and tapered portion 154 is angled to generally correspond to the interior of mid-section portion of spacer 152.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A device for attaching a fixation element to bone comprising:
   a handle;
   an elongated holding sleeve having proximal and distal ends defining a channel therebetween, the sleeve supported by the handle and movable from a distally extended position to a proximal position at least partially retracted into the handle, the distal end of the sleeve defining a tip configured to releaseably hold the fixation element; and
   a driver shaft having a distal end defining a solid tip portion configured to abuttingly contact the fixation element, the shaft axially slideable inside the sleeve from a first position in which the tip portion is withdrawn from the distal end of the sleeve to a second position in which the tip portion projects beyond the distal end of the sleeve,
   wherein the shaft is movable to the second position with a fixation element held in the sleeve to eject the fixation element from the sleeve.

2. The device of claim 1, wherein the tip portion is blunt.

3. The device of claim 1, further comprising a spring biasing the sleeve towards the distal position.

4. The device of claim 3, further comprising a tubular cover attached to the handle and having an aperture therein through which the shaft extends, the spring disposed at least partially in the cover.

5. The device of claim 1, wherein the sleeve includes resilient prongs releaseably attaching the sleeve to handle.

6. The device of claim 5, wherein the handle includes a ridge at a distal end configured to engage the sleeve prongs.

7. The device of claim 6, wherein at least a portion of the shaft adjacent the sleeve prongs has a diameter less than the sleeve to define an annular gap, wherein the gap allows the sleeve to be depressed radially inwards to disengage the prongs from the ridge for releasing the sleeve from handle.

8. The device of claim 5, wherein the handle further comprises a tubular cover extending distally from the handle, the sleeve prongs releasably engaging the cover.

9. The device of claim 1, wherein the proximal end of the sleeve includes a resilient member and the handle is configured to releasably engage the member.

10. The device of claim 9, wherein the sleeve and shaft define an annular gap therebetween allowing the resilient member is movable in a radially inwards direction towards the gap to release the sleeve from the handle.

11. The device of claim 1, further comprising a means for releaseably retaining the sleeve in the handle.

12. The device of claim 1, wherein the fixation element is a surgical tack having a head and a shaft, the head being larger in diameter than the shaft.

13. A device for attaching a fixation element to bone comprising:
    a handle;
    an elongated holding sleeve having proximal and distal ends defining a channel therebetween, the sleeve supported by the handle and movable in response to a proximally directed force on the sleeve from a first position distally extended from the handle to a second position at least partially retracted proximally into the handle, the distal end of the sleeve defining a tip configured to releaseably hold the fixation element;
    a spring biasing the sleeve towards the first position; and
    a driver shaft attached to the handle and axially slideable inside the sleeve, the shaft having a distal end defining a solid tip portion configured to abuttingly contact the fixation element, the tip portion at least partially recessed inside the sleeve when the sleeve is in the second position;
    wherein with a fixation element held in the sleeve, the tip portion of the shaft projects beyond the sleeve when the sleeve is moved from the first position to the second position to eject the fixation element from the sleeve.

14. The device of claim 13, wherein the tip portion is blunt.

15. The device of claim 13, wherein the proximal end of the sleeve includes a resilient portion releaseably coupling the sleeve to the handle.

16. The device of claim 13, further comprising a tubular cover attached to the handle and having an aperture therein through which the shaft extends, the spring disposed at least partially in the cover.

17. The device of claim 13, wherein the sleeve includes resilient prongs releaseably attaching the sleeve to handle.

18. The device of claim 17, wherein the handle includes a ridge at a distal end configured to engage the sleeve prongs.

19. The device of claim 18, wherein at least a portion of the shaft adjacent the sleeve prongs has a diameter less than the sleeve to define an annular gap, wherein the gap allows the sleeve to be depressed radially inwards to disengage the prongs from the ridge for releasing the sleeve from handle.

20. The device of claim 1, wherein the fixation element is a surgical tack having a head and a shaft, the head being larger in diameter than the shaft.

21. A device for attaching a fixation element to bone comprising:
    a handle;
    an elongated holding sleeve having proximal and distal ends defining a channel therebetween, the sleeve movable in response to a proximally directed force on the sleeve from a first distal position to a second proximal position at least partially retracted into the handle, the distal end of the sleeve defining a tip configured to releaseably hold the fixation element, the proximal end of the sleeve having a resilient portion bendable in a radial direction to releaseably engage the handle; and a driver shaft attached to the handle and axially slideable inside the sleeve from a proximal position to a distal position, the shaft having a distal end defining a solid tip portion configured to abuttingly contact the fixation element;

wherein with a fixation element held in the sleeve, the tip portion of the shaft projects beyond the sleeve when the shaft is moved to the distal position to contact and eject the fixation element from the sleeve.

22. The device of claim 21, wherein the tip portion is blunt.

23. The device of claim 21, wherein the resilient portion of the sleeve includes prongs.

24. The device of claim 23, wherein the prongs are configured to engage an annular ridge defined by the handle that prevents axially removing the sleeve from the handle without radially bending the prongs.

25. The device of claim 24, wherein the ridge is disposed in a distal end of a tubular member that extends distally from the handle.

26. The device of claim 21, further comprising a spring biasing the sleeve towards the first position.

27. The device of claim 23, further comprising an annular gap between the proximal end of the sleeve adjacent the prongs and the shaft, the prongs bendable radially inwards into the gap to disengage the sleeve from the handle.

28. The device of claim 21, wherein the resilient portion of the sleeve includes prongs that are configured to engage an annular ridge in the handle that prevents axially removing the sleeve from the handle without radially bending the prongs.

* * * * *